United States Patent
Gomez

[19]

[11] Patent Number: 6,042,568

[45] Date of Patent: Mar. 28, 2000

[54] PATIENT MOUNTED I/V PROTECTOR APPARATUS

[76] Inventor: Roy C. Gomez, 537 Linwood Dr., Richland, Va. 24641

[21] Appl. No.: 09/162,742

[22] Filed: Sep. 29, 1998

Related U.S. Application Data

[63] Continuation-in-part of application No. 29/023,798, Jun. 1, 1994, Pat. No. Des. 404,817, which is a continuation of application No. 07/801,124, Dec. 2, 1991, abandoned.

[51] Int. Cl.⁷ ..................................................... A61M 5/32
[52] U.S. Cl. ..................... 604/174; 604/179; 128/DIG. 6
[58] Field of Search ..................................... 604/174, 179; 602/5, 12, 21; 128/877–879, DIG. 6

[56] References Cited

U.S. PATENT DOCUMENTS

| | | | |
|---|---|---|---|
| 3,010,452 | 11/1961 | Smith | 128/133 |
| 3,722,508 | 3/1973 | Roberts | 128/133 |
| 4,198,989 | 4/1980 | Hawke et al. | 128/675 |
| 4,286,588 | 9/1981 | Lovegrove | 128/133 |
| 4,316,461 | 2/1982 | Marais et al. | 128/214 R |
| 4,798,199 | 1/1989 | Hubbard et al. | 128/87 R |
| 4,846,807 | 7/1989 | Safadago | 604/179 |
| 4,862,904 | 9/1989 | West et al. | 128/877 |
| 4,870,976 | 10/1989 | Denny | 128/877 |
| 4,915,097 | 4/1990 | West | 128/77 |
| 4,945,925 | 8/1990 | Garcia | 128/877 |
| 5,131,412 | 7/1992 | Rankin | 128/877 |
| 5,254,078 | 10/1993 | Carter et al. | 602/21 |
| 5,336,179 | 8/1994 | Ryan | 604/80 |
| 5,339,834 | 8/1994 | Marcelli | 128/877 |
| 5,509,902 | 4/1996 | Raulerson | 604/175 |
| 5,577,516 | 11/1996 | Schaeffer | 128/877 |

*Primary Examiner*—Corrine McDermott
*Assistant Examiner*—Cris Rodriguez

[57] ABSTRACT

An I/V protector apparatus includes a first limb reception portion which includes a front. end, a front cushion located at the front end, a rear end, a rear cushion located at the rear end, a main first limb reception region located between the front end and the rear end, and first connectors attached to the main first limb reception region. A second limb reception portion is registrable with the first limb reception portion, and the second limb reception portion includes second connectors for connecting with the first connectors of the first limb reception portion. The first limb reception portion is located below the second limb reception portion when a patient's forearm is received therein. Hooks are connected to the second limb reception portion and project inwardly thereof. The first connectors are first hook-or-loop connectors, and the second connectors are complimentary second loop-or-hook connectors. The I/V protector apparatus is used to prevent an I/V needle from being interfered with or disturbed by a patient, especially a child. With another embodiment of the invention, the second limb reception portion includes a front cushion and a rear cushion. Also, an identification plate is attached to the first limb reception portion.

6 Claims, 6 Drawing Sheets

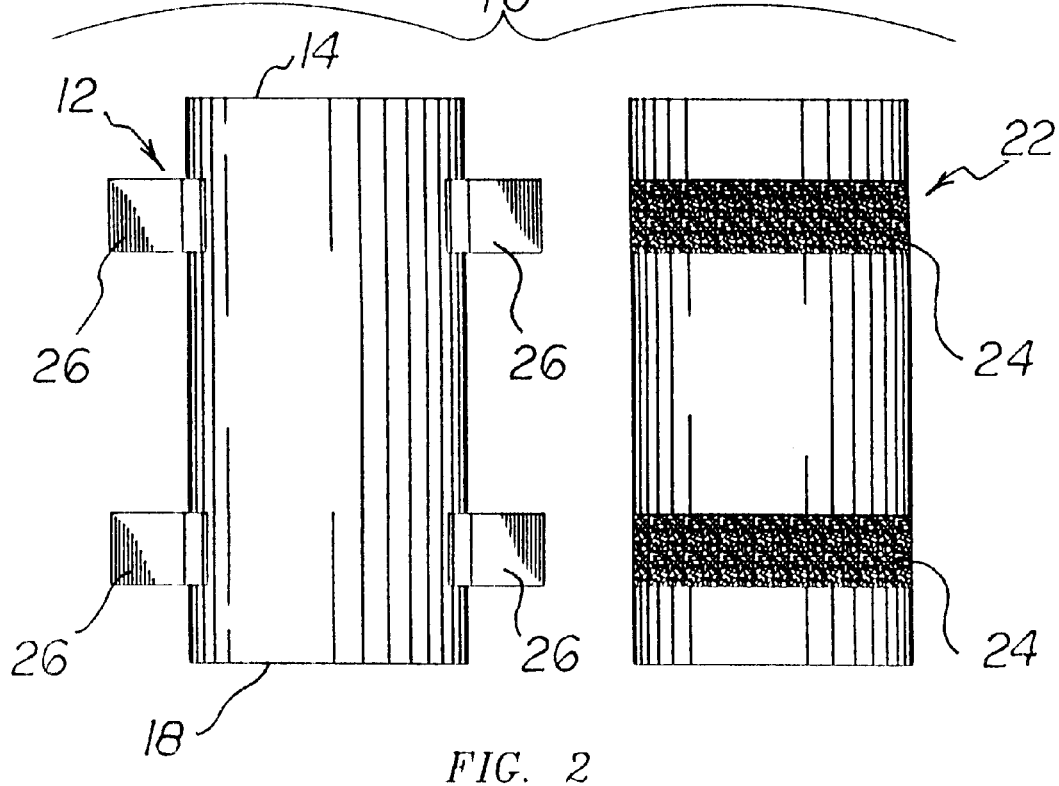
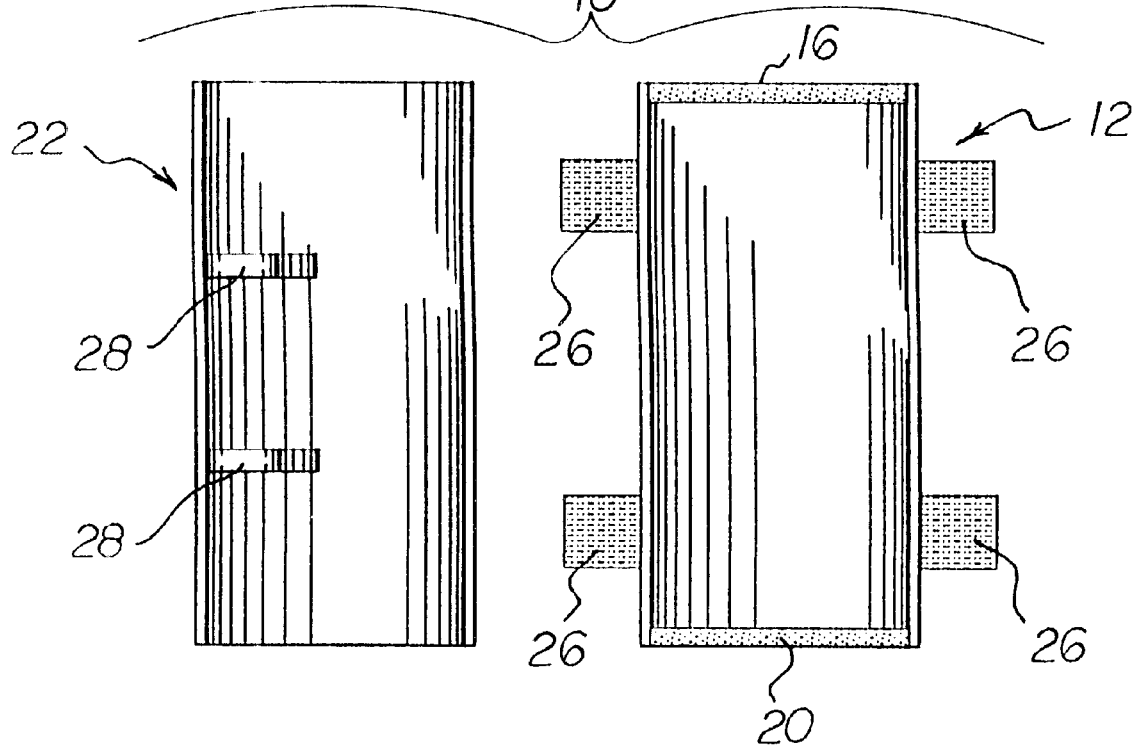

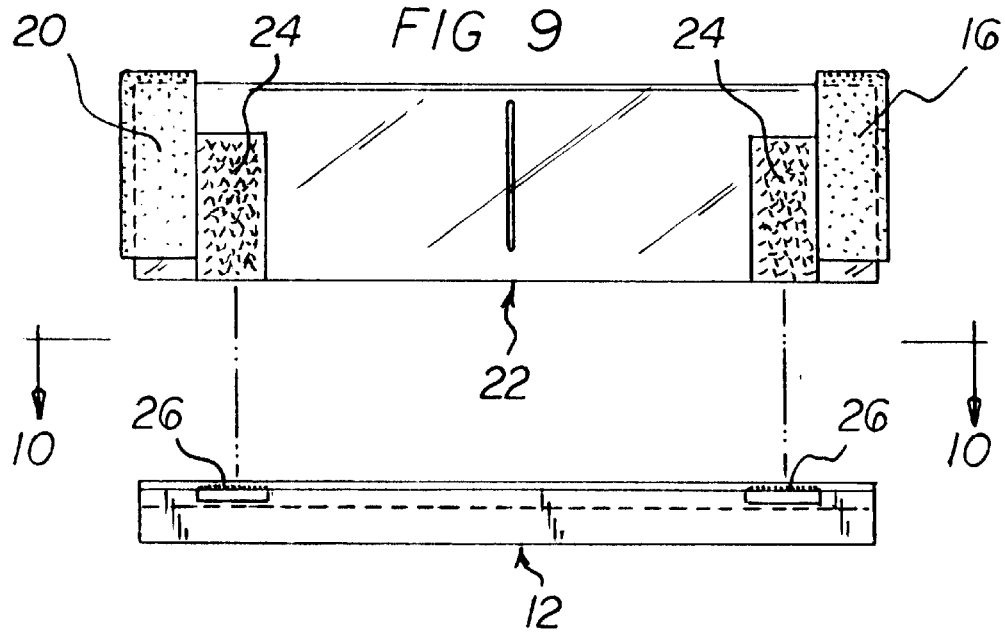
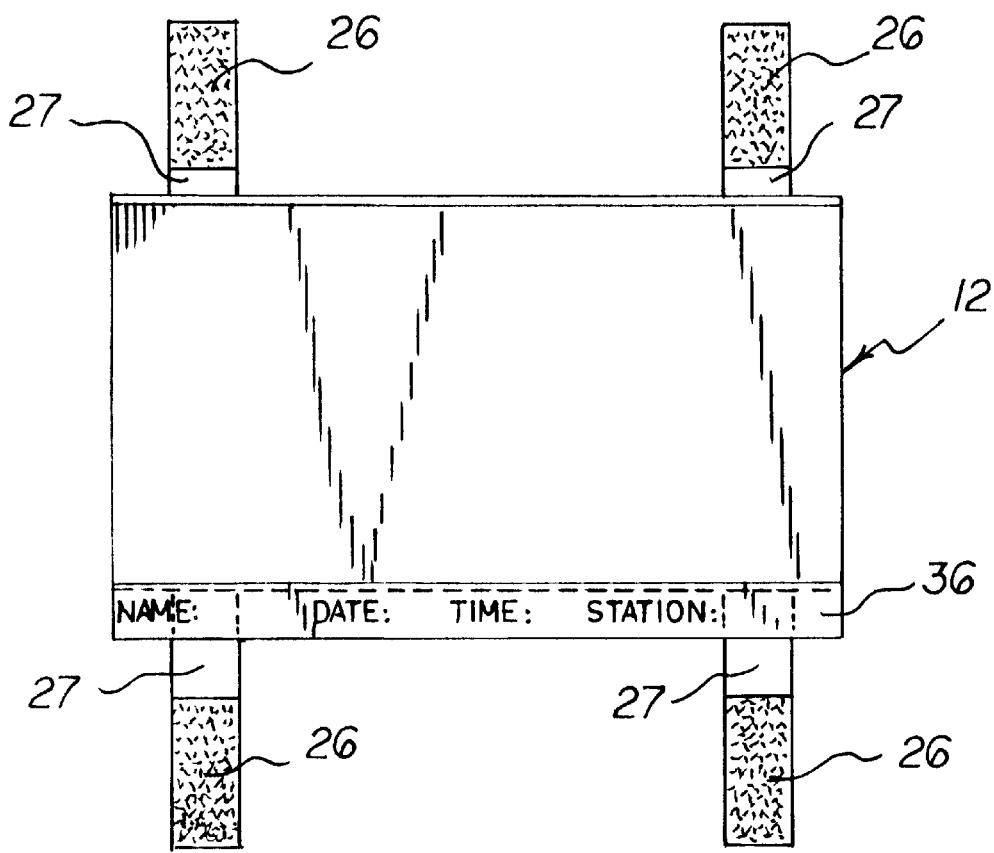

PATIENT MOUNTED I/V PROTECTOR APPARATUS

CROSS-REFERENCE TO RELATED APPLICATION

This application is a continuation-in-part of my prior application Ser. No. 29/023,798; filed Jun. 1, 1994, now U.S. Pat. No. D404,817 which in turn, is a continuation of application Ser. No. 07/801,124; filed Dec. 2, 1991, now abandoned.

BACKGROUND OF THE INVENTION

1. Field of the Invention

The present invention relates generally to intravenous (I/V) administration apparatus, and, more particularly, to I/V apparatus especially adapted for retaining an I/V needle in a desired position on a patient's extremity.

2. Description of the Prior Art

When an I/V needle is in a patient's extremity, such as a patient's arm, it is important that the I/V needle not be moved or dislodged from its intravenous position in the patient. Patients who are children often have a special propensity for disturbing an I/V needle from its desired intravenous position. In this respect, it would be desirable if a device were provided that can be used with young patients to retain an I/V needle in a desired intravenous position.

Presently, to retain an I/V needle in a desired intravenous position in a patient's forearm, a hard board splint is placed under the forearm, and a portion of the I/V apparatus, the patient's forearm, and the splint are taped together. Yet, even with this splint technique, the portion of the I/V needle that is outside the patient's arm can be touched or disturbed by the patient. In this respect, it would be desirable if a device were provided that covers the portion of the I/V needle that is outside the patient's arm so as to prevent the patient from touching or disturbing the I/V needle.

Another difficulty that may arise from using the splint technique just described is related to the accessibility to the patient of the portion of the I/V line that is near the I/V needle. If the portion of the I/V line that is near the I/V needle is pulled, such pulling may disturb the portion of the I/V needle that is in the patient. In this respect, it would be desirable if a device were provided that protects the portion of the I/V line that is adjacent to the I/V needle from being pulled by the patient.

Even if the portion of the I/V line adjacent to the I/V needle is protected from interference by the patient, there is the possibility that if the I/V line is pulled on a significant distance away from the I/V needle, the pulling force can be transmitted through the I/V line to the I/V needle. To prevent such forces on the I/V line from being transmitted along the I/V line to the I/V needle, it would be desirable if a device were provided that blocks a distal pulling force on an I/V line from being transmitted through the I/V line to the I/V needle.

Still other features would be desirable in a patient mounted I/V protector apparatus. For example, it would be desirable if an I/V protector apparatus could be easily fixed to an removed from a patient's forearm. It would also be desirable if an I/V protector apparatus were ornamented with attractive decorations, such as cartoon characters, which are appealing to children. Also, it would be desirable if an I/V protector apparatus could be written upon to receive personalized messages or signatures of friends and loved ones.

Thus, while the foregoing indicates it to be well known to use a splint to protect an I/V needle in a patient, the foregoing does not teach or suggest a patient mounted I/V protector apparatus which has the following combination of desirable features: (1) can be used with young patients to retain an I/V needle in a desired intravenous position; (2) covers the portion of the I/V needle that is outside the patient's arm so as to prevent the patient from touching or disturbing the I/V needle; (3) protects the portion of the I/V line that is adjacent to the I/V needle from being pulled by the patient; (4) blocks a distal pulling force on an I/V line from being transmitted through the I/V line to the I/V needle; (5) can be easily fixed to an removed from a patient's forearm; (6) can be ornamented with attractive decorations, such as cartoon characters, which are appealing to children; and (7) can be written upon to receive personalized messages or signatures of friends and loved ones. The foregoing desired characteristics are provided by the unique patient mounted I/V protector apparatus of the present invention as will be made apparent from the following description thereof. Other advantages of the present invention over the prior art also will be rendered evident.

SUMMARY OF THE INVENTION

To achieve the foregoing and other advantages, the present invention, briefly described, provides an I/V protector apparatus which includes a first limb reception portion which includes a front end, a front cushion located at the front end, a rear end, a rear cushion located at the rear end, a main first limb reception region located between the front end and the rear end, and first connectors attached to the main first limb reception region. A second limb reception portion is registrable with the first limb reception portion, and the second limb reception portion includes second connectors for connecting with the first connectors of the first limb reception portion. The first limb reception portion is located below the second limb reception portion when a patient's forearm is received therein. Hooks are connected to the second limb reception portion and project inwardly thereof. The first connectors are first hook-or-loop connectors, and the second connectors are complimentary second loop-or-hook connectors. The I/V protector apparatus is used to prevent an I/V needle from being interfered with or disturbed by a patient, especially a child. With another embodiment of the invention, the second limb reception portion includes a front cushion and a rear cushion. Also, an identification plate is attached to the first limb reception portion.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In this respect, before explaining at least two preferred embodiments of the invention in detail, it is understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

It is therefore an object of the present invention to provide a new and improved patient mounted I/V protector apparatus which has all of the advantages of the prior art and none of the disadvantages.

It is another object of the present invention to provide a new and improved patient mounted I/V protector apparatus which may be easily and efficiently manufactured and marketed.

It is a further object of the present invention to provide a new and improved patient mounted I/V protector apparatus which is of durable and reliable construction.

An even further object of the present invention is to provide a new and improved patient mounted I/V protector apparatus which is susceptible of a low cost of manufacture with regard to both materials and labor, and which accordingly is then susceptible of low prices of sale to the consuming public, thereby making such patient mounted I/V protector apparatus available to the buying public.

Still yet a further object of the present invention is to provide a new and improved patient mounted I/V protector apparatus which can be used with young patients to retain an I/V needle in a desired intravenous position.

Still another object of the present invention is to provide a new and improved patient mounted I/V protector apparatus that covers the portion of the I/V needle that is outside the patient's arm so as to prevent the patient from touching or disturbing the I/V needle.

Yet another object of the present invention is to provide a new and improved patient mounted I/V protector apparatus which protects the portion of the I/V line that is adjacent to the I/V needle from being pulled by the patient.

Even another object of the present invention is to provide a new and improved patient mounted I/V protector apparatus that blocks a distal pulling force on an I/V line from being transmitted through the I/V line to the I/V needle.

Still a further object of the present invention is to provide a new and improved patient mounted I/V protector apparatus which can be easily fixed to an removed from a patient's forearm.

Yet another object of the present invention is to provide a new and improved patient mounted I/V protector apparatus that can be ornamented with attractive decorations, such as cartoon characters, which are appealing to children.

Still another object of the present invention is to provide a new and improved patient mounted I/V protector apparatus which can be written upon to receive personalized messages or signatures of friends and loved ones.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawing wherein:

FIG. 1 includes a respective bottom and top view of outside portions of respective first and second portions of a first embodiment of the patient mounted I/V protector apparatus of the invention, wherein the first portion includes cushions.

FIG. 2 includes respective top views of inside portions of the respective second and first portions of the first embodiment of the invention shown in FIG. 1.

FIG. 9 is an exploded side view of the embodiment of the invention shown in FIG. 8 wherein the first portion is separated from the second portion.

FIG. 10 is an inside top view of the first portion of the embodiment of the invention shown in FIG. 9 taken along line 10—10 thereof.

DESCRIPTION OF THE PREFERRED EMBODIMENT

With reference to the drawings, a new and improved patient mounted I/V protector apparatus embodying the principles and concepts of the present invention will be described.

Figure 3:
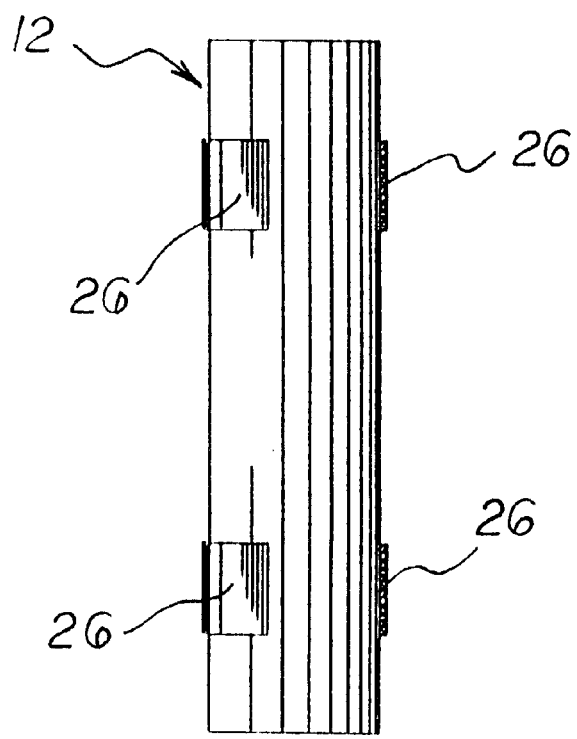
FIG. 3 is a side view of the first portion of the embodiment of the patient mounted I/V protector apparatus of FIGS. 1 and 2.
Figure 4:
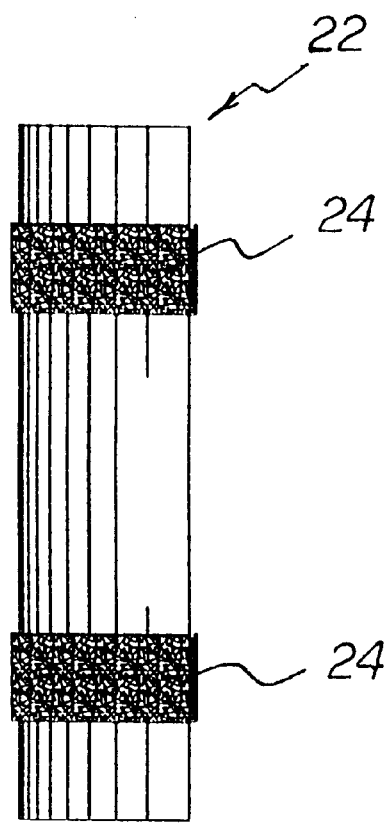
FIG. 4 is a side view of the second portion of the embodiment of the patient mounted I/V protector apparatus of FIGS. 1 and 2.
Figure 5:
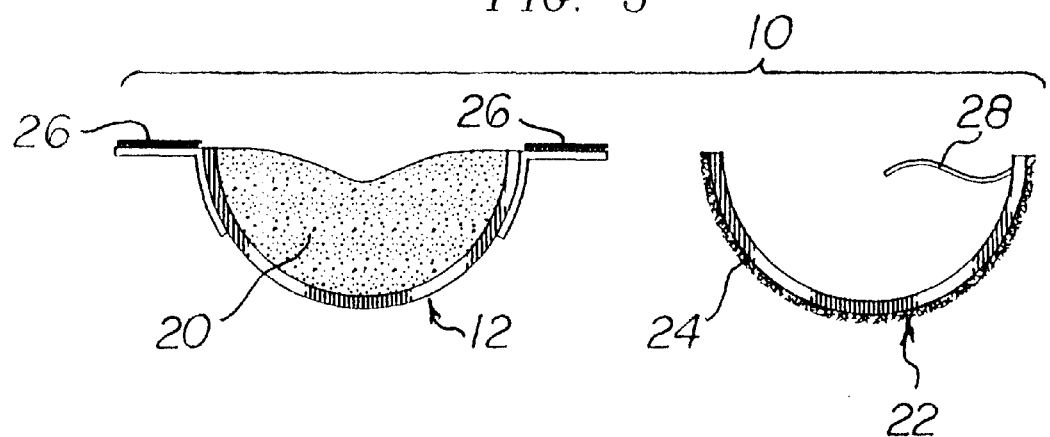
FIG. 5 includes end views of the respective first and second portions of the first embodiment of the invention shown in FIG. 1, wherein the inside of each of the respective first and second portions are facing upward.
Figure 6:
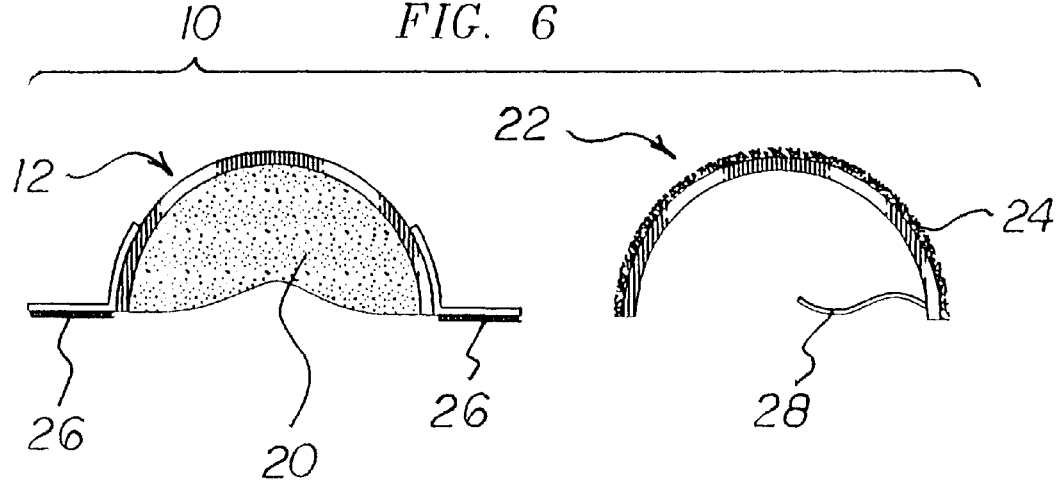
FIG. 6 includes end views of the respective first and second portions of the first embodiment of the invention shown in FIG. 5, wherein the inside of each of the respective first and second portions are facing downward.

Turning to FIGS. 1–6, there is shown a first embodiment of the patient mounted I/V protector apparatus of the invention generally designated by reference numeral 10. In the first embodiment, the patient mounted I/V protector apparatus 10 includes a first limb reception portion 12 which includes a front end 18, a front cushion 20 located at the front end 18, a rear end 14, a rear cushion 16 located at the rear end 14, a main first limb reception region located between the front end 18 and the rear end 14, and first connectors attached to the main first limb reception region. A second limb reception portion 22 is registrable with the first limb reception portion 12, and the second limb reception portion 22 includes second connectors for connecting with the first connectors of the first limb reception portion 12. The first limb reception portion 12 is located below the second limb reception portion 22 when a patient's forearm 30 is received therein. Hooks 28 are connected to the second limb reception portion 22 and project inwardly thereof. The first connectors are first hook-or-loop connectors 26, and the second connectors are complimentary second loop-or-hook connectors 24. The first hook-or-loop connectors 26 and the second loop-or-hook connectors 24 can be made from well known VELCRO(TM) materials. The I/V protector apparatus 10 is used to prevent an I/V needle from being interfered with or disturbed by a patient, especially a child.

It readily will be appreciated that with respect to the embodiment of FIG. 1–6, the first limb reception portion 12 is adapted to be placed under the bottom of a forearm or other limb of an individual, and the second limb reception portion 22 is adapted to be placed over the top of the forearm or other limb in registration with the first limb reception portion. However, if desired, this arrangement obviously can be reversed. That is, the second limb reception portion 22 can be placed on the bottom of a limb, and the first limb reception portion 12 can be placed over the top of the individual's forearm or other limb.

Figure 7:
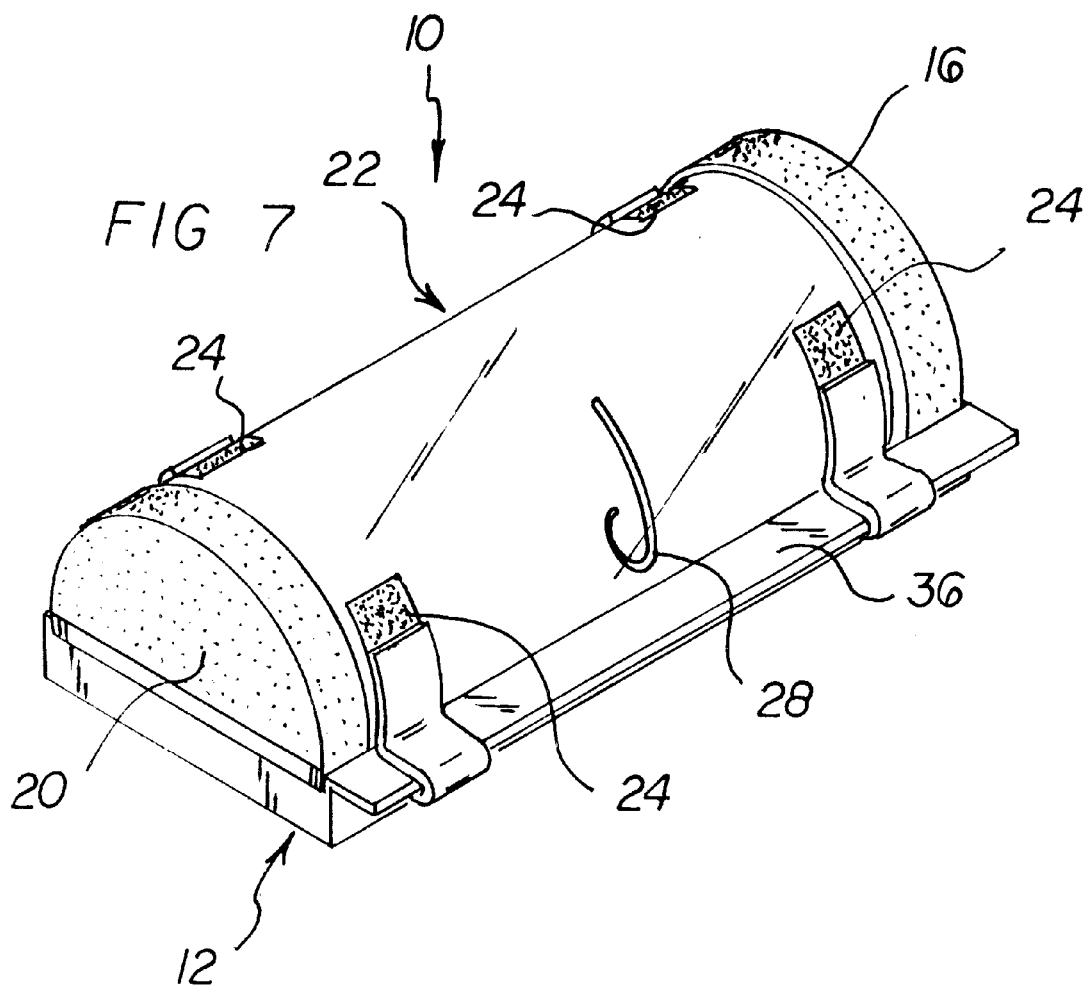
FIG. 7 is a perspective view of a second embodiment of the invention wherein the first portion of the invention has a flat bottom and has a region for patient identification and wherein the second portion includes cushions.
Figure 8:
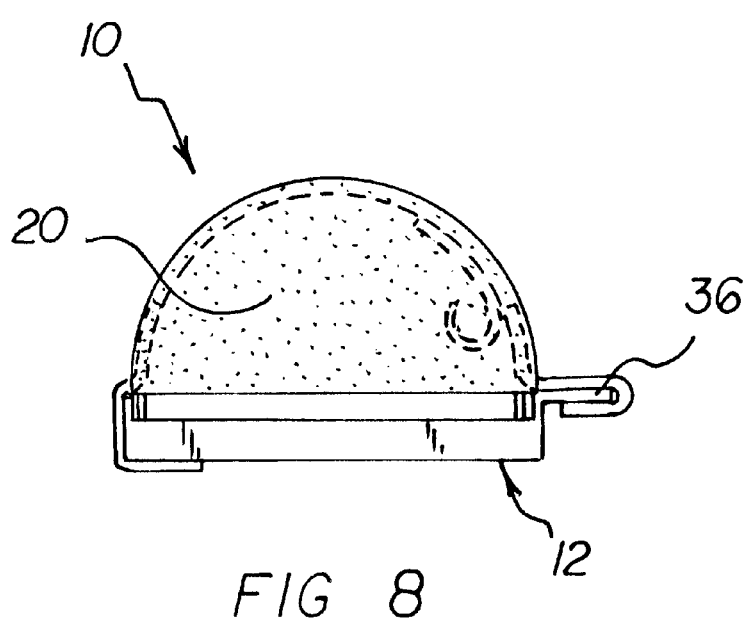
FIG. 8 is an end view of the embodiment of the invention shown in FIG. 7.
Figure 11:
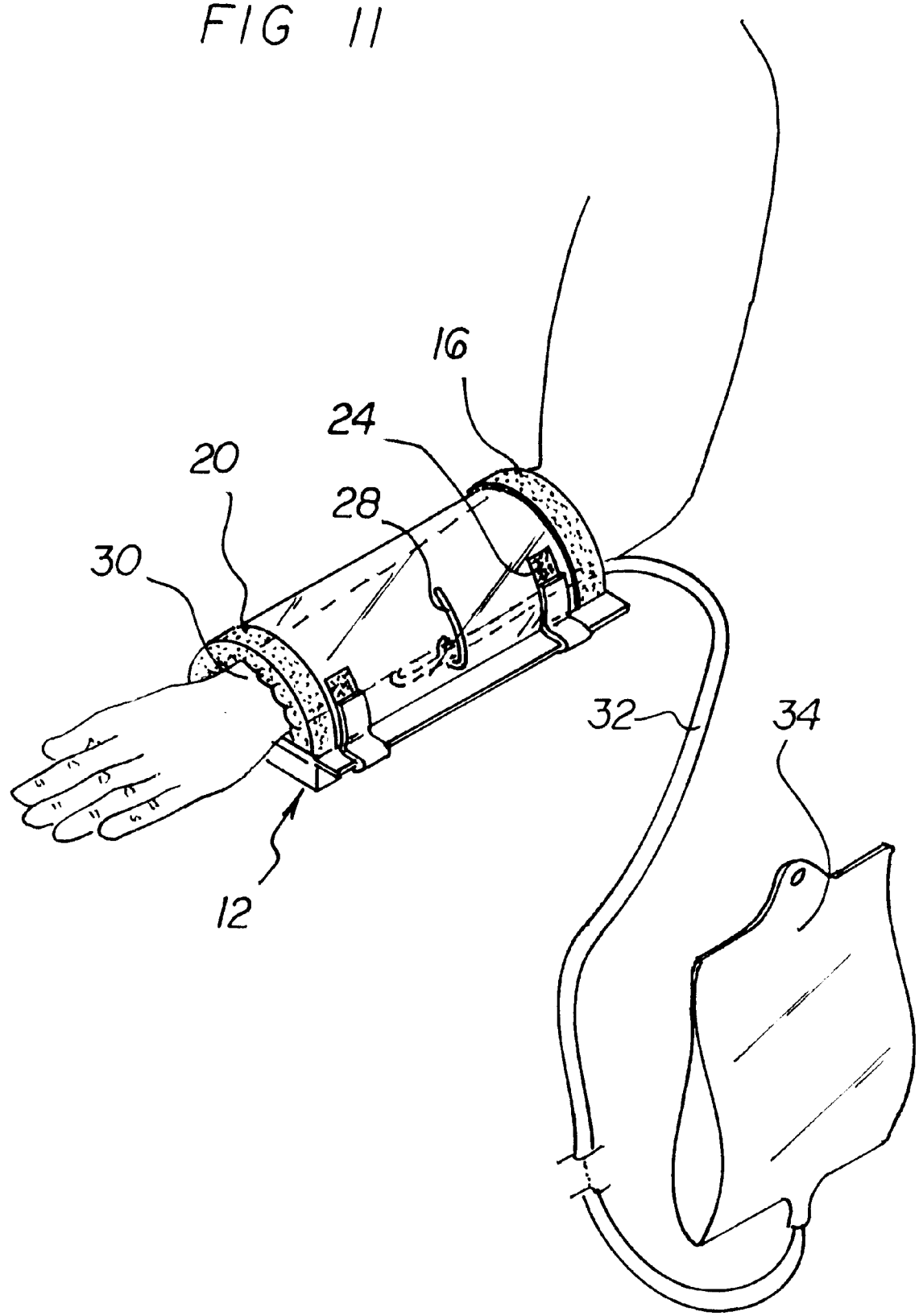
FIG. 11 is a perspective view of the second embodiment of the invention in use on a patient's forearm protecting an I/V needle and line.

Turning to FIGS. 7–11, a second embodiment of the invention is shown. Reference numerals are shown that correspond to like reference numerals that designate like elements shown in the other figures. In addition, with the second embodiment of the invention, the second limb reception portion 22 includes a front cushion 20 and a rear cushion 16. An identification plate 36 is attached to the first limb reception portion 12. As shown most clearly in FIG. 10, the identification plate 36 includes identifying indicia, and the identification plate 36 projects transversely out from a top portion of the first limb reception portion 12. As shown in FIGS. 7–11, the first hook-or-loop connectors 26 are located on flexible tabs 27 which are attached to the first limb reception portion 12. The flexible tabs 27 are bent around the identification plate 36 in order to attach the first hook-or-loop connectors 26 to the second loop-or-hook connectors 24.

Although the physical dimensions of the components of the invention can be selected has any desirable sizes, it has been found that a generally flat first limb reception portion 12, such as shown in FIGS. 7–11 can be 4 inches wide, 8 inches long, and ½ inch thick. The identification plate 36 can be ¼ inch wide, and the identifying indicia can includes name, date, time, and station. The wall thickness of the first limb reception portion 12 can be ⅛ thick. With respect to the second limb reception portion 22, the flexible tabs 27 can be 1½ inches long and ¾ inch wide. To be registrable with the first limb reception portion 12, the second limb reception portion 22 can be 8 inches long and 4 inches wide. The overall shape of the second limb reception portion 22 can be semi-circular, and the second limb reception portion 22 can be made of rigid clear plastic. The front cushion 20 and the rear cushion 16 can be made from resilient plastic foam material. The hooks 28 can be positioned on the second limb reception portion 22 on a side of the second limb reception portion 22 that is opposite to the vicinity of the identification plate 36.

To use the embodiment of the invention illustrated in FIGS. 7–11, a needle (not shown) of an I/V set is introduced into a blood vessel of a patient's forearm 30. The I/V needle is connected to an I/V line or tube 32, which is connected to a bag 34. The forearm 30 is rested on the first limb reception portion 12 so that the portion of the forearm 30 near the wrist rests on the front cushion 20, and the portion of the forearm 30 near the elbow rests on the rear cushion 16. Then, the second limb reception portion 22 is lowered towards the first limb reception portion 12. A portion of the I/V line or tube 32 adjacent to the I/V needle is threaded between the hooks 28, and the second limb reception portion 22 is placed on the first limb reception portion 12 in registration therewith. Then, the first hook-or-loop connectors 26 are connected with the second loop-or-hook connectors 24. In this way, the second limb reception portion 22 is secured to the first limb reception portion 12, and the patient's forearm 30 containing an I/V needle inserted therein is enclosed inside a protection chamber defined by the first limb reception portion 12 and the second limb reception portion 22. In this way, the I/V protector apparatus 10 is mounted on the forearm 30 of the patient. If a pulling force is applied longitudinally to the I/V line or tube 32, the hooks 28 prevent that pulling force from being transmitted to the I/V needle so that the I/V needle is not disturbed by the pulling force.

Thus far, the I/V protector apparatus 10 of the invention has been disclosed to be used on a patient's forearm. However, it is understood that in principle, the I/V protector apparatus 10 of the invention can be mounted generally on any limb, such as, for example, a patient's leg.

The components of the patient mounted I/V protector apparatus of the invention can be made from inexpensive and durable plastic materials.

As to the manner of usage and operation of the instant invention, the same is apparent from the above disclosure, and accordingly, no further discussion relative to the manner of usage and operation need be provided.

It is apparent from the above that the present invention accomplishes all of the objects set forth by providing a new and improved patient mounted I/V protector apparatus that is low in cost, relatively simple in design and operation, and which may advantageously be used with young patients to retain an I/V needle in a desired intravenous position. With the invention, a patient mounted I/V protector apparatus is provided which covers the portion of the I/V needle that is outside the patient's arm so as to prevent the patient from touching or disturbing the I/V needle. With the invention, a patient mounted I/V protector apparatus is provided which protects the portion of the I/V line that is adjacent to the I/V needle from being pulled by the patient. With the invention, a patient mounted I/V protector apparatus is provided which blocks a distal pulling force on an I/V line from being transmitted through the I/V line to the I/V needle. With the invention, a patient mounted I/V protector apparatus is provided which can be easily fixed to an removed from a patient's forearm. With the invention, a patient mounted I/V protector apparatus is provided which can be ornamented with attractive decorations, such as cartoon characters, which are appealing to children. With the invention, a patient mounted I/V protector apparatus is provided which can be written upon to receive personalized messages or signatures of friends and loved ones.

The designation "I/V" as used herein and in the appended claims means "intravenous" as is well recognized in the art of medicine.

Thus, while the present invention has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein, including, but not limited to, variations in size, materials, shape, form, function and manner of operation, assembly and use.

Hence, the proper scope of the present invention should be determined only by the broadest interpretation of the appended claims so as to encompass all such modifications as well as all relationships equivalent to those illustrated in the drawings and described in the specification.

Finally, it will be appreciated that the purpose of the annexed Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

What is claimed as being new and desired to be protected by Letters Patent of the United States is as follows:

1. An I/V protector apparatus, comprising:
   a first limb reception portion which includes a front end, a front cushion located at said front end, a rear end, a rear cushion located at said rear end, a main first limb reception region located between said front end and said rear end, and first connectors attached to said main first limb reception region, and
   a second limb reception portion which is registrable with said first limb reception portion, wherein said second limb reception portion includes second connectors for connecting with said first connectors of said first limb reception portion,
   further including:
      at least one hook member connected to said second limb reception portion and protecting inwardly thereof.

2. The apparatus of claim 1 wherein said first connectors are first hook-or-loop connectors and said second connectors are complimentary second loop-or-hook connectors.

3. The apparatus of claim 1 wherein said second limb reception portion includes a front cushion and a rear cushion.

4. An I/V protector apparatus, comprising:
   a first limb reception portion which includes a front end, a front cushion located at said front end, a rear end, a rear cushion located at said rear end, a main first limb reception region located between said front end and said rear end, and first connectors attached to said main first limb reception region, and
   a second limb reception portion which is registrable with said first limb reception portion, wherein said second limb reception portion includes second connectors for connecting with said first connectors of said first limb reception portion;
   further including:
      an identification plate attached to said first limb reception portion.

5. The apparatus of claim 4 wherein said first connectors are first hook-or-loop connectors and said second connectors are complimentary second loop-or-hook connectors.

6. The apparatus of claim 4 wherein said second limb reception portion includes a front cushion and a rear cushion.

* * * * *